United States Patent
Bui et al.

(10) Patent No.: US 9,078,835 B2
(45) Date of Patent: Jul. 14, 2015

(54) COMPOSITION CONTAINING AN AQUEOUS DISPERSION OF POLYURETHANE AND AN OIL-SOLUBLE POLAR MODIFIED POLYMER

(75) Inventors: Hy Si Bui, Piscataway, NJ (US); Mohamed Kanji, Edison, NJ (US); Chunhua Li, North Plainfield, NJ (US); Bruno Thierry Bavouzet, Gentilly (FR); Shoham Bhadra, North Brunswick, NJ (US)

(73) Assignee: L'Oreal, Paris (FR)

( * ) Notice: Subject to any disclaimer, the term of this patent is extended or adjusted under 35 U.S.C. 154(b) by 319 days.

(21) Appl. No.: 12/971,301

(22) Filed: Dec. 17, 2010

(65) Prior Publication Data
US 2011/0150806 A1    Jun. 23, 2011

Related U.S. Application Data

(60) Provisional application No. 61/287,926, filed on Dec. 18, 2009, provisional application No. 61/287,905, filed on Dec. 18, 2009.

(51) Int. Cl.
| A61Q 1/00 | (2006.01) |
| A61K 8/87 | (2006.01) |
| A61Q 1/10 | (2006.01) |
| A61K 8/39 | (2006.01) |
| A61K 8/81 | (2006.01) |
| A61K 8/84 | (2006.01) |
| A61K 8/92 | (2006.01) |

(52) U.S. Cl.
CPC ... *A61K 8/87* (2013.01); *A61K 8/39* (2013.01); *A61K 8/8111* (2013.01); *A61K 8/8164* (2013.01); *A61K 8/84* (2013.01); *A61K 8/92* (2013.01); *A61Q 1/10* (2013.01)

(58) Field of Classification Search
None
See application file for complete search history.

(56) References Cited

U.S. PATENT DOCUMENTS

| 4,871,536 | A | 10/1989 | Arraudeau et al. |
| 6,475,495 | B1 * | 11/2002 | Maignan et al. ............ 424/401 |
| 6,482,400 | B1 * | 11/2002 | Collin ........................ 424/70.6 |
| 6,492,455 | B1 | 12/2002 | Nadolsky |
| 7,445,770 | B2 | 11/2008 | Berezkin et al. |
| 2002/0081322 | A1 * | 6/2002 | Lawson et al. ............. 424/401 |
| 2005/0268405 | A1 * | 12/2005 | Brun et al. ..................... 8/405 |
| 2008/0097070 | A1 | 4/2008 | Nguyen et al. |
| 2008/0226569 | A1 * | 9/2008 | Berezkin et al. ............ 424/59 |
| 2009/0016982 | A1 | 1/2009 | Raineau et al. |
| 2009/0022678 | A1 | 1/2009 | Berezkin et al. |
| 2009/0142289 | A1 * | 6/2009 | Arditty et al. .............. 424/70.7 |
| 2009/0169501 | A1 * | 7/2009 | Feng et al. ................. 424/70.7 |
| 2011/0097289 | A1 | 4/2011 | Viala et al. |
| 2011/0300088 | A1 * | 12/2011 | Bui et al. .................... 424/64 |

FOREIGN PATENT DOCUMENTS

| EP | 1 064 920 A1 | 1/2001 |
| EP | 1 281 385 A1 | 2/2003 |
| EP | 2 105 126 A1 | 9/2009 |
| WO | WO 98/16196 A1 | 4/1998 |
| WO | WO 2009/085783 A1 | 7/2009 |
| WO | WO 2010/068888 A2 | 6/2010 |
| WO | WO 2010/068888 A3 | 6/2010 |

OTHER PUBLICATIONS

BRIJ72, http://pubchem.ncbi.nlm.nih.gov/summary/summary.cgi?sid=24849850&viewopt=PubChem, accessed Feb. 9, 2012.*
BRIJ78, http://www.sciencelab.com/msds.php?msdsId=9923139, accessed Feb. 9, 2012.*
Extended European Search Report issued Jul. 25, 2011, in Patent Application No. 10195611.8.
Office Action issued Aug. 29, 2011, in European Patent Application No. 10195611.8.
Sophie Viala, "Filming agent gives eyes a striking look", Cosmetics Spray Technology Marketing, www.cossma.com, XP 002599685, Apr. 2009, pp. 36-38.
"New Baycusan C product line: Five new ingredients for looking great", BayerMaterialScienceNAFTA.com, XP 002595522, May 21, 2009, pp. 1-3.
U.S. Appl. No. 12/971,255, filed Dec. 17, 2010, Bui.
U.S. Appl. No. 12/971,323, filed Dec. 17, 2010, Bui.
European Office Action Issued Jan. 9, 2013 in Patent Application No. 10 195 611.8.

* cited by examiner

*Primary Examiner* — Kortney L Klinkel
*Assistant Examiner* — Melissa Javier
(74) *Attorney, Agent, or Firm* — Oblon, McClelland, Maier & Neustadt, L.L.P.

(57) ABSTRACT

The invention relates to a composition comprising at least one aqueous polyurethane dispersion, at least one oil-soluble polar modified polymer, at least one alkoxylated fatty alcohol, and at least one polyamine compound having at least two amine groups.

23 Claims, No Drawings

US 9,078,835 B2

COMPOSITION CONTAINING AN AQUEOUS DISPERSION OF POLYURETHANE AND AN OIL-SOLUBLE POLAR MODIFIED POLYMER

CROSS-REFERENCE TO RELATED APPLICATIONS

This application claims the benefit of priority under 35 U.S.C. §119(e) from U.S. Provisional Application Ser. Nos. 61/287,926 and 61/287,905, both filed Dec. 18, 2009, the entire contents of which are hereby incorporated by reference.

FIELD OF THE INVENTION

The present invention relates to compositions comprising at least one aqueous dispersion of polyurethane and at least one oil-soluble polymer modified polymer. The compositions further comprise at least one alkoxylated fatty alcohol and at least one polyamine compound having at least two amine groups. The compositions have beneficial cosmetic properties including but not limited to good smudge resistance, good volumizing properties, good curling properties, good curl retention properties, and the ability to be easily removed with water.

DISCUSSION OF THE BACKGROUND

In the past, long-wear, smudge-resistant mascaras were not washable with water. Such mascaras were typically anhydrous.

In contrast, mascara compositions which were washable with water were not long-wear or smudge-resistant. Such mascaras typically contained significant amounts of water (for example, oil-in-water emulsions).

Given these countervailing considerations, it has been difficult to prepare long-wear, smudge-resistant mascaras which are washable with water.

Thus, there remains a need for improved mascara compositions which have desired wear properties as well as desired removal properties.

SUMMARY OF THE INVENTION

The present invention relates to compositions comprising at least one aqueous polyurethane dispersion, at least one oil-soluble polar modified polymer, at least one alkoxyated fatty alcohol, and at least one polyamine compound having at least two amine groups.

The present invention relates to compositions comprising (i) at least one aqueous polyurethane dispersion, and (ii) a reaction product of at least one oil-soluble polar modified polymer, at least one alkoxylated fatty alcohol, and at least one polyamine compound having at least two amine groups.

The present invention relates to compositions comprising (i) at least one aqueous polyurethane dispersion, (ii) at least one alkoxyated fatty alcohol, and (iii) a reaction product of at least one oil-soluble polar modified polymer, and at least one polyamine compound having at least two amine groups.

The present invention relates to compositions made by combining ingredients comprising at least one aqueous polyurethane dispersion, at least one oil-soluble polar modified polymer, at least one alkoxylated fatty alcohol, and at least one polyamine compound having at least two amine groups.

The present invention relates to compositions comprising at least one aqueous polyurethane dispersion, at least one oil-soluble polar modified polymer, at least two alkoxyated fatty alcohols, and at least one polyamine compound having at least two amine groups.

The present invention relates to compositions comprising (i) at least one aqueous polyurethane dispersion, and (ii) a reaction product of at least one oil-soluble polar modified polymer, at least two alkoxyated fatty alcohols, and at least one polyamine compound having at least two amine groups.

The present invention relates to compositions comprising (i) at least one aqueous polyurethane dispersion, (ii) at least two alkoxyated fatty alcohols, and (iii) a reaction product of at least one oil-soluble polar modified polymer, and at least one polyamine compound having at least two amine groups.

The present invention relates to compositions made by combining ingredients comprising at least one aqueous polyurethane dispersion, at least one oil-soluble polar modified polymer, at least two alkoxyated fatty alcohols, and at least one polyamine compound having at least two amine groups.

The present invention also relates to the above compositions further comprising a desired agent such as a colorant, styling agent and/or pharmacologically active agent.

The present invention relates to hair colorant or styling compositions as described above.

The present invention relates to mascara compositions as described above.

The present invention also relates to methods of treating, caring for and/or making up keratinous material (for example, hair, skin, eyelashes or lips) by applying cosmetic compositions of the present invention to the keratinous material in an amount sufficient to treat, care for and/or make up the keratinous material.

The present invention also relates to methods of improving the smudge-resistance properties of a cosmetic composition upon application to a keratin material, and/or the adhesion, volumizing, long-wear and/or transfer-resistance properties of a cosmetic composition, and/or the curling or curl retention properties of a cosmetic composition, comprising adding to a composition at least one aqueous polyurethane dispersion, at least one oil-soluble polar modified polymer, at least one alkoxyated fatty alcohol, and at least one polyamine compound having at least two amine groups.

The present invention also relates to methods of improving the smudge-resistance properties of a cosmetic composition upon application to a keratin material, and/or the adhesion, volumizing, long-wear and/or transfer-resistance properties of a cosmetic composition, and/or the curling or curl retention properties of a cosmetic composition, comprising adding to a composition at least one aqueous polyurethane dispersion, at least one oil-soluble polar modified polymer, at least two alkoxyated fatty alcohols, and at least one polyamine compound having at least two amine groups.

The present invention also relates to methods of removing mascara from eyelashes comprising removing the mascara compositions described above from eyelashes by applying water to the mascara composition in an amount sufficient to remove the composition from the eyelashes.

The present invention also relates to methods of making a composition comprising reacting at least one aqueous polyurethane dispersion, at least one oil-soluble polar modified polymer, at least one alkoxyated fatty alcohol, and at least one polyamine compound having at least two amine groups to form the composition.

The present invention also relates to methods of making a composition comprising reacting at least one aqueous polyurethane dispersion, at least one oil-soluble polar modified polymer, at least two alkoxyated fatty alcohols, and at least one polyamine compound having at least two amine groups to form the composition.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

The compositions and methods of the present invention can comprise, consist of, or consist essentially of the essential elements and limitations of the invention described herein, as well as any additional or optional ingredients, components, or limitations described herein or otherwise useful.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; prop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemcial Co., poly (ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the polar modified polymer(s) represent from about 1% to about 30% of the total weight of the composition, more preferably from about 3% to about 20% of the total weight of the composition, and most preferably from about 5% to about 15%, including all ranges and subranges therebetween.

Aqueous Polyurethane Dispersion

According to the present invention, compositions comprising at least one aqueous polyurethane dispersion are provided. "Aqueous polyurethane dispersion" as used herein means the aqueous polyurethane dispersions disclosed in U.S. Pat. No. 7,445,770 and/or U.S. Pat. No. 7,452,770, the entire contents of both of which are hereby incorporated by reference.

More specifically, the aqueous polyurethane dispersions of the present invention are preferably the reaction products of:

A) a prepolymer according to the formula:

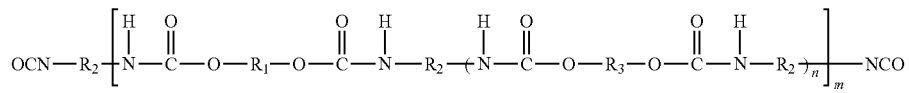

wherein $R_1$ represents a bivalent radical of a dihydroxyl functional compound, $R_2$ represents a hydrocarbon radical of an aliphatic or cycloaliphatic polyisocyanate, $R_3$ represents a radical of a low molecular weight diol, optionally substituted with ionic groups, n is from 0 to 5, and m is >1;

B) at least one chain extender according to the formula: $H_2N$—$R_4$—$NH_2$ wherein $R_4$ represents an alkylene or alkylene oxide radical not substituted with ionic or potentially ionic groups; and C) at least one chain extender according to the formula: $H_2N$—$R_5$—$NH_2$ wherein $R_5$ represents an alkylene radical substituted with ionic or potentially ionic groups.

Suitable dihydroxyl compounds for providing the bivalent radical $R_1$ include those having two hydroxy groups and having number average molecular weights of from about 700 to about 16,000, and preferably from about 750 to about 5000. Examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates are preferred. Mixtures of various such compounds are also within the scope of the present invention.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate and isophorone diisocyanate.

"Low molecular weight diols" in the context of $R_3$ means diols having a molecular weight from about 62 to 700, preferably 62 to 200. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxyphenyl)propane), hydrogenated bisphenol A (2,2-bis(4-hydroxycyclohexyl)propane), and mixtures thereof. Optionally, the low molecular weight diols may contain ionic or potentially ionic groups. Suitable lower molecular weight diols containing ionic or potentially ionic groups are those disclosed in U.S. Pat. No. 3,412,054, the contents of which is hereby incorporated by reference. Preferred compounds include dimethylol butanoic acid (DMBA), dimethylol propionic acid (DMBA) and carboxyl-containing caprolactone polyester diol. If lower molecular weight diols containing ionic or potentially ionic groups are used, they are preferably used in an amount such that <0.30 meq of COOH per gram of polyurethane in the polyurethane dispersion are present.

The prepolymer is chain extended using two classes of chain extenders. First, compounds having the formula: $H_2N$—$R_4$—$NH_2$ wherein $R_4$ represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxy)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1, 3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders are compounds having the formula: $H_2N-R_5-NH_2$ wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS) or the sodium salt of N-(2-aminoethyl)-2-aminopropionic acid.

The polyurethane according to the invention may also include compounds which are situated in each case at the chain ends and terminate said chains (chain terminators) as described in U.S. Pat. No. 7,445,770 and/or U.S. Pat. No. 7,452,770.

Preferably, the aqueous polyurethane dispersion has a viscosity of less than 2000 mPa·s at 23° C., preferably less than 1500, preferably less than 1000, including all ranges and subranges therebetween.

Also preferably, the aqueous polyurethane dispersion has a solids content based on the weigh of the dispersion of from 20% to 60%, preferably from 25% to 55% and preferably from 30% to 50%, including all ranges and subranges therebetween.

Suitable aqueous polyurethane dispersions for use in the present invention include, but are not limited to, aqueous polyurethane dispersions sold under the BAYCUSAN® name by Bayer such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane-35).

According to preferred embodiments, the at least one aqueous polyurethane dispersion is present in the composition of the present invention in an amount ranging from about 1 to 35% by weight, more preferably from about 2 to about 30% by weight, more preferably from about 3 to about 20% by weight based on the total weight of the composition, including all ranges and subranges within these ranges.

Alkoxylated Fatty Alcohol

According to the present invention, compositions comprising at least one alkoxylated fatty alcohol are provided. According to preferred embodiments of the present invention, compositions comprising at least two alkoxylated fatty alcohols are provided. "Alkoxylated fatty alcohol" as used herein means a compound having at least one fatty portion (8 carbon atoms or more) and at least one alkoxylated portion ($-(CH_2)_nO-$, where n is an integer from 1 to 5, preferably 2 to 3). According to particularly preferred embodiments, the alkoxylated fatty alcohols of the present invention can be used as non-ionic surfactants, if desired. In this regard, the alkoxylated fatty alcohols of the present invention preferably have an HLB (hydrophilic-lipophilic balance) value from 1-20, including all ranges and subranges therebetween, with HLB values ranging from 1 to 5 (particularly 3 to 5) or from 15-20 (particularly 16 to 18) being most preferred.

The alkoxylated fatty alcohol can be present in the composition of the present invention in the water and/or oil phase.

Preferably, the alkoxylated fatty alcohol can be chosen from di-alkyl, tri-alkyl- and combinations of di-alkyl and tri-alkyl substituted ethoxylated polymers. They can also be chosen from mono-alkyl, di-alkyl, tri-alkyl, tetra-alkyl substituted alkyl ethoxylated polymers and all combinations thereof. The alkyl group can be saturated or unsaturated, branched or linear and contain a number of carbon atoms preferably from about 12 carbon atoms to about 50 carbon atoms, including all ranges and subranges therebetween, for example, 20 to 40 carbon atoms, 22 to 24 carbon atoms, 30 to 50 carbon atoms, and 40 to 60 carbon atoms. Most preferably, the fatty portion contains a mixture of compounds of varying carbon atoms such as, for example, C20-C40 compounds, C22-C24 compounds, C30-050 compounds, and C40-C60 compounds.

Preferably, the alkoxylated portion of the alkoxylated fatty alcohols of the present invention contain 2 or more alkoxylation units, preferably from 10 to 200 alkoxylation units, preferably from 20 to 150 alkoxylation units, and preferably from 25 to 100 alkoxylation units, including all ranges and subranges therebetween. Also preferably, the alkoxylation units contain 2 carbon atoms (ethoxylation units) and/or 3 carbon atoms (propoxylation units).

The amount of alkoxylation can also be determined by the percent by weight of the alkoxylated portion with respect to the total weight of the compound. Suitable weight percentages of the alkoxylated portion with respect to the total weight of the compound include, but are not limited to, 10% to 95%, preferably 20% to 90%, including all ranges and subranges therebetween with 75% to 90% (particularly 80% to 90%) or 20% to 50% being preferred.

Preferably, the alkoxylated fatty alcohols of the present invention have a number average molecular weight (Mn) greater than 500, preferably from 500 to 5,000, including all ranges and subranges therebetween such as, for example, Mn of 500 to 1250 or an Mn of 2,000 to 5,000.

The alkyl substitution of the alkoxylated fatty alcohol can include mono-alkyl, di-alkyl, tri-alkyl and tetra-alkyl substitution of the polymer and combinations thereof. Suitable examples of mono alkyl substituted polymers include: Steareth-100 available as Brij 700 from Uniqema Inc., Pareth alcohols available as Performathox 450, 480 and 490 available from New Phase Technologies, Inc. Suitable examples of di-alkyl substituted polymers include PEG 120 methyl glucose dioleate available as Glutamate DOE-120 and Glucamate DOE-120 both from Chemron Corporation. Suitable examples of tri-alkyl substituted polymers include PEG 120 methyl glucose trioleate available as Glucamate LT from Chemron Corporation. Suitable examples of tetra-alkyl substituted polymers include PEG 150 pentaerythrityl tetrastearate available as Crothix from Croda Corporation.

Suitable alkoxylated fatty alcohols for use in the present invention include, but are not limited to, alkoxylated C20-C40 fatty alcohols sold under the PERFORMATHOX® name by New Phase Technologies such as, for example, PERFORMATHOX® 420 ETHOXYLATE (Mn=575; 20% by weight ethoxylation), PERFORMATHOX® 450 ETHOXYLATE (Mn=920; 50% by weight ethoxylation), PERFORMATHOX® 480 ETHOXYLATE (Mn=2300; 80% by weight ethoxylation), PERFORMATHOX® 490 ETHOXYLATE (Mn=4600; 90% by weight ethoxylation), PERFOR- MATHOX® 520 ETHOXYLATE (Mn=690; 20% by weight ethoxylation), and PERFORMATHOX® 550 ETHOXYLATE (Mn=1100; 50% by weight ethoxylation).

According to preferred embodiments, the at least one alkoxyated fatty alcohol is present in the composition of the present invention in an amount ranging from about 0.5 to 40% by weight, more preferably from about 2 to about 30% by weight, more preferably from about 5% to about 20% based on the total weight of the composition, including all ranges and subranges within these ranges.

According to preferred embodiments where at least two alkoxylated fatty alcohols are present, at least one alkoxylated fatty alcohol has a Mn from 500 to 1,250 and/or no more than 50% alkoxylation by weight (preferably both), and at least one alkoxylated fatty alcohol has a Mn from 2,500 to 5,000 and/or 75% to 90% alkoxylation (preferably both). So, for example, preferred combinations of alkoxylated fatty alcohols include: Performathox 420 and Performathox 490; and Performathox 520 and Performathox 490. Preferably, compositions of the present invention comprise more alkoxylated fatty alcohol having a higher Mn and/or a higher alkoxylation content than fatty alcohol having a lower Mn and/or a lower alkoxylation content. Preferably, the weight ratio of higher Mn and/or alkoxylation content fatty alcohol to lower Mn and/or alkoxylation content fatty alcohol is from 5:1 to about 1:1, preferably from 3:1 to 2:1. Alternatively, the ratios could be inverse of those previously set forth, preferably from 1:5 to about 1:1, preferably from 1:2 to 1:3.

The alkoxylated fatty alcohol can added to the water or oil phase of a composition. If added to the oil phase, the alkoxylated fatty alcohol can result in a smooth, creamy texture with fast product deposition. If added to the water phase, the alkoxylated fatty alcohol can result in a slightly rougher texture. Preferably, the lower hydrophile lipophile balance (HLB) valued alkoxylated fatty alcohols (e.g. Performathox 420) are added to the oil phase, while the higher hydrophile lipophile balance (HLB) valued alkoxylated fatty alcohols (e.g. Performathox 490) are added to the water phase.

According to particularly preferred embodiments, the compositions of the present invention contain more alkoxylated fatty alcohol than aqueous polyurethane dispersion on a weight basis. Particularly preferred compositions include alkoxylated fatty alcohol to aqueous polyurethane dispersion in a weight ratio of between 10:1 and 5:1 (for example, 9:1, 8:1, 7:1 and 6:1), including all ranges and subranges therebetween. However, the compositions may also contain more aqueous polyurethane dispersion than alkoxylated fatty alcohol on a weight basis in the same preferred ratios discussed above (1:10, 1:5, etc.).

Polyamine Compound

According to the present invention, compositions comprising at least one polyamine compound are provided. In accordance with the present invention, the polyamine compound has at least two primary amine groups available to react with hydrophilic groups of the oil-soluble polar modified polymer.

According to particularly preferred embodiments, the polyamine compound is a polyalkyleneimine, preferably a C2-C5 polyalkyleneamine compound, more preferably a polyethyleneimine or polypropyleneimine. Most preferably, the polyalkylenamine is polyethyleneimine ("PEI"). The polyalkyleneamine compound preferably has an average molecular weight range of from 500-200,000, including all ranges and subranges therebetween.

According to preferred embodiments, compositions of the present invention contain polyethyleneimine compounds in the form of branched polymers. Commercially available examples of such polymers are available from BASF under the tradename LUPASOL or POLYIMIN. Non-limiting examples of such polyethyleneimines include Lupasol® PS, Lupasol® PL, Lupasol® PR8515, Lupasol® G20, Lupasol® G35.

According to other embodiments of the present invention, polyamines such as polyethyleneimines and polypropyleneimines can be in the form of dendrimers. Non-limiting examples of such dendrimers are manufactured by the company DSM, and/or are disclosed in U.S. Pat. No. 5,530,092 and U.S. Pat. No. 5,610,268, the contents of which are hereby incorporated by reference. Commercially available examples of such polymers include polyamidoamine or polypropyleneimine polymers from DENDRITECH sold under the STARBURST® name.

According to other embodiments of the present invention, derivatives of polyalkyleneamines are suitable polyamines. Such derivatives include, but are not limited to, alkylated derivatives, the addition products of alkylcarboxylic acids to polyalkyleneamines, the addition products of ketones and of aldehydes to polyalkyleneamines, the addition products of isocyanates and of isothiocyanates to polyalkyleneamines, the addition products of alkylene oxide or of polyalkylene oxide block polymers to polyalkyleneamines, quaternized derivatives of polyalkyleneamines, the addition products of a silicone to polyalkyleneamines, and copolymers of dicarboxylic acid and polyalkyleneamines. Even further suitable polymamines include, but are not limited to, polyvinylimidazoles (homopolymers or copolymers), polyvinylpyridines (homopolymers or copolymers), compounds comprising vinylimidazole monomers (see, for example, U.S. Pat. No. 5,677,384, hereby incorporated by reference), and polymers based on amino acids containing a basic side chain (preferably selected from proteins and peptides comprising at least 5%, preferably at least 10% of amino acids selected from histidine, lysine and arginine). Such suitable polyamines as described above include those disclosed and described in U.S. Pat. No. 6,162,448, the contents of which are hereby incorporated by reference. Commercially available examples of such polymers include polyvinylamine/formamide such as those sold under the Lupamine® name by BASF, chitosan from vegetable origin such as those sold under the Kiosmetine® or Kitozyme® names, or copolymer 845 sold by ISP.

According to preferred embodiments, the at least one polyamine compound is present in the composition of the present invention in an amount ranging from about 0.05 to about 20% by weight, preferably from about 0.25 to about 10% by weight, preferably from about 0.3 to about 5% by weight, preferably from about 0.5 to about 3% by weight, based on the total weight of the composition, including all ranges and subranges within these ranges.

Preferably, the amount of polyamine compound reacted with the oil-soluble polar modified polymer is such that at least two amine groups on the polyamine compound react with the oil-soluble polar modified polymer to form links or bonds between the amine groups and the hydrophilic groups of the oil-soluble polar modified polymer. The appropriate amount of polyamine compound to react with the oil-soluble polar modified polymer to obtain a reaction product can be easily determined, taking into account the number/amount of reactive amine groups on the polyamine compound and the number/amount of corresponding reactive groups on the oil-soluble polar modified polymer (for example, maleic anhydride groups). According to preferred embodiments, excess oil-soluble polar modified polymer (as determined by the relative number/amount of corresponding reactive groups on the polymer as compared to the reactive amine groups on the polyamine) is reacted with polyamine. Preferably, the polyamine to oil-soluble polar modified ratio is between 0.005 and 1, preferably between 0.006 and 0.5, and preferably between 0.007 and 0.1, including all ranges and subranges therebetween.

According to preferred embodiments, the at least one polyamine compound is present in the composition of the present invention in an amount ranging from about 0.25 to about 10% by weight, preferably from about 0.3 to about 5% by weight, preferably from about 0.5 to about 3% by weight, based on the total weight of the composition, including all ranges and subranges within these ranges.

Reaction Product

According to preferred embodiments of the present invention, the oil-soluble polar modified polymer is reacted with the polyamine compound, in the presence of water in, at minimum, an amount sufficient to solubilize the polyamine, to form a reaction product. In accordance with the preferred embodiments, the reaction product is water-insoluble.

Although not wanting to be bound by any particular theory, it is believed that at a temperature below 100° C., the reaction of the oil-soluble polar modified polymer with the primary amine group of the polyamine opens the anhydride ring to form a half acid and half amide crosslinked product. However, at a temperature above 100° C., the reaction of the oil-soluble polar modified polymer with the primary amine group of the polyamine opens the anhydride ring to form an imide crosslinked product. The former product is preferred over the latter product. It is not necessary for all amine groups and all hydrophilic groups to react with each other to form the reaction product. Rather, it is possible that the composition may contain free polyamine and/or free oil-soluble polar modified polymer in addition to the reaction product.

Although not wanting to be bound by any particular theory, it is also believed that the polyamine(s) can be non-covalently assembled with the polar modified polymer(s) by electrostatic interaction between an amine group of the polyamine and a hydrophilic group (for example, carboxylic acid group associated with maleic anhydride groups) of the polar modified polymer to form a supramolecule. For example, with specific reference to maleic anhydride groups, in the presence of water these groups can open to form dicarboxylic acid groups which can interact with protonated primary amines of the polyamine through ionic interaction to form a polymer-polymer complex with hydrophilic core crosslinkers and a hydrophobic network that act as supramolecular capsule. If a large amount of maleic anhydride groups are present, the secondary amine groups of polyamine are also protonated and interact with alkyl carboxylates.

According to preferred embodiments, the oil-soluble polar modified polymer is in an oil carrier, and the polyamine compound is in an aqueous carrier, and the reaction occurs by combining the oil carrier and the aqueous carrier. Because the oil-soluble polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C.

Without intending to be bound by any particular theory, it is believed that the reason for this is that due to the chemical and physical reactions which take place when the oil-soluble polar modified polymer is combined with the polyamine, the subsequent reaction product that is formed is surprisingly and unexpectedly able to entrap large amounts of water molecules within its hydrophobic matrix. The resultant product is eminently capable of forming a film, is self-emulsifying, water-proof. Moreover, the product is both stable and capable of carrying various types of ingredients.

According to other preferred embodiments of the present invention, the oil-soluble polar modified polymer is reacted with the alkoxylated fatty alcohol, in the presence of oil to form a reaction product. If the reaction is conducted at a relatively high temperature (for example, above 140° C.) and for a long period of time (>5 hours), a significant amount of the hydrophilic group (for example, carboxylic acid group associated with maleic anhydride groups) of the oil soluble polar modified polymer reacts with hydroxyl group(s) of the alkoxylated fatty alcohol to yield a significant amount of the reaction product. If, however, the reaction is conducted at a relatively low temperature (for example, below 100° C.) and for a short period of time (<1 hour), only a small portion of the hydrophilic group of the polar modified polymer reacts with hydroxyl group(s) of the alkoxylated fatty alcohol to yield a minor amount of reaction product. Depending upon desired application, a minor amount or a significant amount of the reaction product may be desired.

In accordance with the above, compositions of the present invention preferably comprise at least one aqueous polyurethane dispersion, at least one oil-soluble polar modified polymer, at least one alkoxyated fatty alcohol, and at least one polyamine compound having at least two amine groups.

Compositions of the present invention can optionally further comprise any additive usually used in the field(s) under consideration. For example, dispersants such as poly(12-hydroxystearic acid), antioxidants, oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, film forming agents, colorants, and mixtures thereof can be added. A non-exhaustive listing of such ingredients can be found in U.S. patent application publication no. 2004/0170586, the entire contents of which are hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

Suitable oils include volatile and/or non-volatile oils. Such oils can be any acceptable oil including but not limited to silicone oils and/or hydrocarbon oils.

According to certain embodiments, the oil carrier comprises one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other embodiments, the oil carrier comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to other embodiments of the present invention, the oil carrier comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalene, squalane, hydrogenated polyisobutene, hydrogenated polydecene, polybutene, mineral oil, pentahydrosqualene, and mixtures thereof.

According to preferred embodiments of the present invention, the compositions can further comprise a desired agent. The desired agent can be, for example, any colorant (pigment, dye, etc.), any pharmaceutically or cosmetically active agent, or any film forming agent known in the art. For example, a cosmetic makeup composition or a paint composition comprising colorant can provide colorant and/or filim forming agent to a substrate (skin, lips, wall, frame, etc.) during use to provide the substrate with the desired film and/or color. Similarly, a pharmaceutical or cosmetic composition comprising a pharmaceutically active agent can provide such active agent to the patient or consumer upon use.

Acceptable colorants include pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

Representative nacreous pigments include white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, Acceptable film forming agents and/or rheological agents are known in the art and include, but are not limited to, those disclosed in U.S. patent application publication no. 2004/0170586, the entire contents of which is hereby incorporated by reference.

Non-limiting representative examples of acceptable film forming/rheolgocial agents include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

Suitable examples of acceptable liposoluble polymers include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Acceptable film forming/rheological agents also include water soluble polymers such as, for example, high molecular weight crosslinked homopolymers of acrylic acid, and Acrylates/C10-30 Alkyl Acrylate Crosspolymer, such as the Carbopol® and Pemulen®; anionic acrylate polymers such as Salcare® AST and cationic acrylate polymers such as Salcare® SC96; acrylamidopropylttrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof.

According to preferred embodiments of the present invention, the compositions comprise substantial amounts of water. Preferably, compositions of the present invention comprise sufficient water to form a water-in-oil emulsion. Preferably, compositions of the present invention comprise from about 5% to about 80% water, more preferably from about 15% to about 60% water, and more preferably from about 20% to about 50% water by weight with respect to the total weight of the composition, including all ranges and subranges therebetween.

In one embodiment of the present invention, the compositions of the present invention are substantially free of silicone oils (i.e., contain less than about 0.5% silicone oils). In another embodiment, the compositions are substantially free of non-silicone oils (i.e., contain less than about 0.5% non-silicone oils). In another embodiment, the compositions are substantially free of non-volatile oils (i.e., contain less than about 0.5% non-volatile oils).

One preferred embodiment of the present invention is an emulsion which is substantially free of surfactant (that is, less than 3% of surfactant), essentially free of surfactant (that is, less than 2% surfactant), or free of surfactant (that is, less than 0.5% surfactant).

Another preferred embodiment of the present invention is a composition which contains so little elastomer that the presence of such elastomer not affect the cosmetic properties of the composition. Preferably, the compositions are substantially free of such elastomers (i.e., contain less than about 0.5% elastomer), essentially free of such elastomers (i.e., contain less than about 0.25% elastomer) or free of such elastomer (i.e., contain no elastomer).

According to other preferred embodiments, methods of treating, caring for and/or enhancing the appearance of keratinous material by applying compositions of the present invention to the keratinous material in an amount sufficient to treat, care for and/or enhance the appearance of the keratinous material are provided. In accordance with these preceding preferred embodiments, the compositions of the present invention are applied topically to the desired area of the keratin material in an amount sufficient to treat, care for and/or enhance the appearance of the keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved waterproof characteristics, improved feel upon application (for example, texture, reduced drag or tackiness), increased anti-smudging properties, shine/color characteristics, increased volume properties and/or increased long wear properties are provided.

According to other embodiments of the present invention, methods of improving the anti-smudging, volumizing, waterproof, transfer-resistance and/or long wear properties of a composition, comprising adding at least one polar modified polymer, at least one polyamine, at least one aqueous polyurethane dispersion, and at least one alkoxylated fatty alcohol to the composition are provided.

According to other embodiments, methods of removing mascara from eyelashes comprising removing a mascara composition of the present invention from eyelashes by applying water to the mascara composition in an amount sufficient to remove the composition from the eyelashes are provided.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Examples 1 and 2

Mascara Compositions

|  | INCI | Inventive Example 1 (weight %) | Inventive Example 2 (weight %) |
|---|---|---|---|
| 1 | Caprylic/capric triglyceride | 1.00 | 1 |
| 2 | C20-40 Pareth-95 (and) polyethylene (Performathox 490) | 10.00 | 10.00 |
| 3 | Polyalkylene/maleic anhydride wax in isohexadecane* | 9.33 | 9.33 |
| 4 | Iron oxides | 8.00 | 8 |
| 5 | Isododecane | 33.42 | 25.72 |
| 6 | Ethylparaben | 0.20 | 0.2 |
| 7 | Water | 26.00 | 19.5 |
| 8 | Disodium EDTA | 0.10 | 0.1 |
| 9 | Potassium cetyl phosphate | 2.00 | 2 |
| 10 | Methyl paraben | 0.35 | 0.35 |
| 11 | Pentylene glycol | 2.00 | 2 |
| 12 | PEI-35 (50% solid/50% water) | 2.00 | 1.2 |
| 13 | Simethicone | 0.10 | 0.1 |
| 14 | Aqueous polyurethane polyester dispersion (Baycusan 1004) (41% solid/59% water) | 5.00 | 20.00 |
| 15 | Phenoxyethanol | 0.50 | 0.5 |

*PP207, which is a linear polypropylene-ethylene-maleic anhydride copolymer wax commercially available from Clariant under the tradename LICOCARE PP207 LP 3349. Material is supplied in 25% insohexadecane.

Procedure

In metal container A, 1-3, 5 and 6 were added and heated until 90° C. (solids melted and became uniform). 4 was added and homogenized at 900 RPM for 1 hour.

In side beaker B, 10 and 11 were mixed, and heated until 70° C. (mixture became clear).

In side tank C with water bath, 7-9 were added, mixed until uniform, and heated until 90° C. Contents of side beaker B were added along with 12.

In side beaker D, 14 was heated to 90° C., and then added to side tank C.

Side tank C was then mixed for 20 minutes.

When both metal container A and side tank C were at the same temperature 85° C., the contents of side tank C were slowly added to metal container A while homogenizing at 500 RPM.

After the mixture was uniform, 13 was added, and the mixture was mixed mechanically with a stirring rod until uniform.

Then, the mixture began to be cooled naturally. 15 was added to the mixture at 55° C. Then, cooling continued to 25° C.

Examples 3 and 4

Comparative Examples

| | Ingredient | Example 3 Amount (weight %) | Example 4 Amount (weight %) |
|---|---|---|---|
| 1 | Caprylic/capric triglyceride | 1.00 | 1 |
| 2 | C20-40 Pareth-95 (and) polyethylene (Performathox 490) | 0 | 10.00 |
| 3 | Polyalkylene/maleic anhydride wax in isohexadecane* | 9.33 | 9.33 |
| 4 | Iron oxides | 8.00 | 8.00 |
| 5 | Isododecane | 40 | 35 |
| 6 | Ethylparaben | 0.20 | 0.2 |
| 7 | Water | 34.42 | 29.42 |
| 8 | Disodium EDTA | 0.10 | 0.1 |
| 9 | Potassium cetyl phosphate | 2.00 | 2 |
| 10 | Methyl paraben | 0.35 | 0.35 |
| 11 | Pentylene glycol | 2.00 | 2 |
| 12 | PEI-35 | 2.00 | 2 |
| 13 | Simethicone | 0.10 | 0.1 |
| 14 | Aqueous polyurethane polyester dispersion (Baycusan 1004) | 0 | 0 |
| 15 | Phenoxyethanol | 0.50 | 0.5 |

Similar mascara compositions were prepared. Example Comparative Composition Example 3 contained a polar modified wax (PP207) and PEI. Comparative Example 4 contained a polar modified wax (PP 207), PEI and an alkoxylated fatty alcohol (Performathox 490). Invention Example 1 contained a polar modified wax (PP 207), PEI, an alkoxylated fatty alcohol (Performathox 490), and an aqueous polyurethane dispersion (Baycusan 1004).

Instrumental evaluation was used to determine volume increase %. An Immersion study regarding the water/oil resistance was used as an indication of wear properties.

For comparative composition example 3, volume increased 299%. For comparative composition example 4, volume increased 611%. For invention example 1, volume increased 683%.

Comparative Example 3 had excellent wear properties (long wear, smudge proof), but did not have good volumizing properties.

Comparative Example 4, on the other hand, had good volume, but not good wear properties.

Surprisingly, Invention Example 1 containing an aqueous polyurethane dispersion contained both good wear properties and good volumizing properties.

Example 5

Mascara Composition

| | Ingredient | Amount (weight %) |
|---|---|---|
| 1 | Caprylic/capric triglyceride | 1.00 |
| 2 | C20-40 Pareth-3 (and) polyethylene (Performathox 420) | 5.00 |
| 3 | Polyalkylene/maleic anhydride wax in isohexadecane* | 9.33 |
| 4 | Iron oxides | 8.00 |
| 5 | Isododecane | 28.42 |
| 6 | Ethylparaben | 0.20 |
| 7 | Water | 24.75 |
| 8 | Disodium EDTA | 0.10 |
| 9 | Potassium cetyl phosphate | 2.00 |
| 10 | Methyl paraben | 0.35 |
| 11 | Pentylene glycol | 2.00 |
| 12 | PEI-35 (50% solid/50% water) | 2.00 |
| 13 | Simethicone | 0.10 |
| 14 | Aqueous polyurethane polyester dispersion (Baycusan 1004) (41% solid/59% water) | 6.25 |
| 15 | Phenoxyethanol | 0.50 |
| 16 | C20-40 Pareth-95 (and) polyethylene (Performathox 490) | 10.00 |

*PP207, which is a linear polypropylene-ethylene-maleic anhydride copolymer wax commercially available from Clariant under the tradename LICOCARE PP207 LP 3349. Material is supplied in 25% insohexadecane Procedure In metal container A, 1-3, 5 and 6 were added and heated until 90° C. (solids melted and became uniform). 4 was added, the mixture was cooled to 75° C., and homogenized at 900 RPM for 1 hour.

In side beaker B, 10 and 11 were mixed, and heated until 70° C. (mixture became clear).

In side tank C with water bath, 7-9 and 16 were added, mixed until uniform, and heated until 70° C. Contents of side beaker B were added along with 12.

In side beaker D, 14 was heated to 70° C., and then added to side tank C.

Side tank C was then mixed for 20 minutes.

When both metal container A and side tank C were at the same temperature 85° C., the contents of side tank C were slowly added to metal container A while homogenizing at 500 RPM.

After the mixture was uniform, 13 was added, and the mixture was mixed mechanically with a stirring rod until uniform.

Then, the mixture began to be cooled naturally. 15 was added to the mixture at 55° C. Then, cooling continued to 25° C.

The composition was a smooth, creamy and shiny mascara that had smudge-resistance and volumizing properties, and at the same time could be easily removed by water. The mascara also provided good curl and curl retention.

What is claimed is:

1. A composition comprising (a) water, (b) at least one aqueous polyurethane dispersion, (c) at least one alkoxylated fatty alcohol, and (d) a first water-insoluble half acid and half amide crosslinked reaction product comprising (1) at least one polyamine compound having at least two amine groups and (2) at least one oil-soluble polar modified polymer comprising at least one C2-C4 monomer and modified with at least one hydrophilic unit, wherein the oil-soluble polar modified polymer has a weight-average molecular weight of less than or equal to 25,000 g/mol and a melting point above 75° C., wherein the composition is in the form of an emulsion and wherein the aqueous polyurethane dispersion comprises a second reaction product of:

A) a prepolymer according to the formula:

$$OCN-R_2-\left[\begin{array}{c}H\ O\\|\ \|\\N-C-O-R_1-O-C-N-R_2-\\\ \ \ \ \ \ \ \ \ \ \ \ \ \ \ \ \ \ \ \ \ \ \ \|\ |\\\ \ \ \ \ \ \ \ \ \ \ \ \ \ \ \ \ \ \ \ \ \ \ O\ H\\\left(N-C-O-R_3-O-C-N-R_2\right)_n\end{array}\right]_m NCO$$

wherein $R_1$ is a bivalent radical of a dihydroxyl functional compound, $R_2$ is a hydrocarbon radical of an aliphatic or cycloaliphatic polyisocyanate, $R_3$ is a radical of a low molecular weight diol, optionally substituted with ionic groups, n is from 0 to 5, and m is >1;

B) at least one chain extender according to the formula: $H_2N-R_4-NH_2$ wherein $R_4$ is an alkylene or alkylene oxide radical not substituted with ionic groups; and C) at least one chain extender according to the formula: $H_2N-R_5-NH_2$ wherein $R_5$ is an alkylene radical substituted with at least one ionic group or at least one potentially ionic group, wherein the polyamine is a branched polyethyleneimine.

2. The composition of claim 1, comprising at least two alkoxylated fatty alcohols.

3. The composition of claim 1, wherein the at least one oil-soluble polar modified polymer is present in an amount of from 1% to 30% of the total weight of the composition.

4. The composition of claim 1, wherein the oil-soluble polar modified polymer is a polypropylene and/or polyethylene-maleic anhydride modified wax.

5. The composition of claim 1, wherein the polyamine is present in an amount of from 0.05% to 20% by weight, based on the weight of the composition.

6. The composition of claim 1, wherein the alkoxylated fatty alcohol(s) is present in an amount of from 0.5% to 40% by weight, based on the weight of the composition.

7. The composition of claim 2, wherein at least one alkoxylated fatty alcohol has an average molecular weight (Mn) from 500 to 1,250 and/or no more than 50% alkoxylation by weight, and at least one alkoxylated fatty alcohol has a Mn from 2,500 to 5,000 and/or 75% to 90% alkoxylation.

8. The composition of claim 7, wherein the weight ratio of the alkoxylated fatty alcohol having the higher Mn and/or alkoxylation content to alkoxylated fatty alcohol having lower Mn and/or alkoxylation content is from 5:1 to 1:5.

9. The composition of claim 8, wherein the weight ratio is from 3:1 to 2:1 or from 1:2 to 1:3.

10. The composition of claim 1, wherein the polyurethane of the at least one aqueous polyurethane dispersion comprises a hydrophilic portion.

11. The composition of claim 1, wherein water is present in an amount of from about 5% to about 50% by weight, based on the weight of the composition.

12. The composition of claim 1, further comprising at least one colorant.

13. The composition of claim 1, wherein the first reaction product further comprises at least one alkoxylated fatty alcohol.

14. The composition of claim 1, in the form of a water-in-oil emulsion.

15. The composition of claim 1, in the form of a mascara.

16. The composition of claim 1, wherein the weight-average molecular weight of the oil-soluble polar modified polymer is from 500 to 10,000 g/mol.

17. The composition of claim 1, wherein the oil-soluble polar modified polymer has from about 5% to about 30% hydrophilic units.

18. The composition of claim 1, wherein the hydrophilic units are maleic anhydride units.

19. The composition of claim 1, wherein $R_2$ is selected from the group consisting of tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane, bis-(4-isocyanatocyclohexyl)-methane, 1,3- and 1,4-bis(isocyanatomethyl)-cyclohexane, bis-(4-isocyanato-3-methyl-cyclohexyl)-methane, 2,4-diisocyanatotoluene, 2,6-diisocyanatotoluene, hydrogenated diisocyanatotoluene, 4,4'-diisocyanato diphenyl methane, 1,5-diisocyanato naphthalene, and mixtures thereof.

20. The composition of claim 19, wherein $R_3$ is selected from the group consisting of ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, 2,2-bis(4-hydroxyphenyl)propane, 2,2-bis(4-hydroxycyclohexyl)propane, dimethylol butanoic acid, dimethylol propionic acid, carboxyl-containing caprolactone polyester diol, and mixtures thereof.

21. The composition of claim 20, wherein the aqueous polyurethane dispersion has a viscosity of less than 2,000 mPa·s at 23° C.

22. The composition of claim 20, wherein the aqueous polyurethane dispersion has a solids content based on the weight of the dispersion of from 20% to 60%.

23. The composition of claim 1, wherein the aqueous polyurethane dispersion has a viscosity of less than 2,000 mPa·s at 23° C. and has a solids content based on the weight of the dispersion of from 20% to 60%.

* * * * *